United States Patent [19]
Goi et al.

[11] Patent Number: 5,279,556
[45] Date of Patent: Jan. 18, 1994

[54] PERISTALTIC PUMP WITH ROTARY ENCODER

[75] Inventors: Nobuaki Goi, Yamatokoriyama, Japan; George A. Bowman, Vernon Hills; Joseph B. Matthews, Grayslake, both of Ill.

[73] Assignees: Sharp Kabushiki Kaisha, Osaka, Japan; Baxter International Inc., Deerfield, Ill.

[21] Appl. No.: 879,357

[22] Filed: May 7, 1992

Related U.S. Application Data

[63] Continuation-in-part of Ser. No. 513,886, Apr. 24, 1990, abandoned.

[30] Foreign Application Priority Data

Apr. 28, 1989 [JP] Japan .................. 1-111230

[51] Int. Cl.⁵ .............................. F04B 49/00
[52] U.S. Cl. .................. 604/67; 128/DIG. 13; 417/18
[58] Field of Search .......... 604/65, 67; 128/DIG. 12, DIG. 13; 417/18

[56] References Cited

U.S. PATENT DOCUMENTS

| | | |
|---|---|---|
| 3,423,591 | 1/1969 | Schrempp. |
| 3,957,377 | 5/1976 | Hutchinson. |
| 4,107,595 | 8/1978 | Campe. |
| 4,233,592 | 11/1980 | Leichle. |
| 4,263,506 | 4/1981 | Epstein. |
| 4,342,025 | 7/1982 | Spalti et al. |
| 4,360,769 | 11/1982 | Selkey et al. |
| 4,423,958 | 1/1984 | Schmitt. |
| 4,602,882 | 7/1986 | Akazawa. |
| 4,628,239 | 12/1986 | Everett, Jr. |
| 4,683,410 | 7/1987 | Kressirer et al. |
| 4,687,981 | 8/1987 | Okada. |
| 4,736,187 | 4/1988 | Kibrick et al. |
| 4,803,354 | 2/1989 | Onodera et al. |
| 4,869,646 | 9/1989 | Gordon et al. |
| 4,899,093 | 2/1990 | Gleim. |

FOREIGN PATENT DOCUMENTS

| | | |
|---|---|---|
| 0066636 | 12/1982 | European Pat. Off. |
| 0090440 | 10/1983 | European Pat. Off. |
| 2948182 | 7/1980 | Fed. Rep. of Germany. |
| 3247313 | 6/1984 | Fed. Rep. of Germany. |
| 59-48616 | 3/1984 | Japan. |
| 59-224516 | 12/1984 | Japan. |
| 60-47916 | 3/1985 | Japan. |
| 60-47917 | 3/1985 | Japan. |
| 60-163938 | 10/1985 | Japan. |

OTHER PUBLICATIONS

"IHI Rotary Encoder," Ishikawajima-Harima Eng. Rev. (Japan), vol. 16, No. 6 (Nov. 1976), pp. 723–731.
Patents Abstract of Japan, vol. 11, No. 126, Apr. 21, 1987, 61-269018.

*Primary Examiner*—Paul J. Hirsch

[57] ABSTRACT

A rotary encoder comprises a rotary plate having a plurality of primary slits defined in the rotary plate in a circular row coaxial with the axis of rotation of the rotary plate. The rotary plate also has at least one reference slit defined therein at a position radially of the circular row of the primary slits. A primary photoelectric detector including a source of light and a photo-sensor positioned one above the other with the circular row of the primary slits intervening therebetween is used to detect the passage of the primary slits therethrough while an auxiliary photoelectric detector including a source of light and a photo-sensor positioned one above the other with the path of travel of the reference slit intervening therebetween is used to detect the passage of the reference slit therethrough.

3 Claims, 3 Drawing Sheets

5,279,556

PERISTALTIC PUMP WITH ROTARY ENCODER

This application is a continuation-in-part of application Ser. No. 07/513,886, filed on Apr. 24, 1990, the entire contents of which are hereby incorporated by reference, now abandoned.

BACKGROUND OF THE INVENTION

1. Field of the Invention

The present invention relates to a rotary encoder.

2. Description of the Prior Art

Conventional rotary encoders comprise a rotary plate having a plurality of slits defined therein and spaced an equal distance from each other in a direction circumferentially thereof. These slits are selectively sensed by a sensor during rotation of the rotary plate to determine the angle of rotation of the rotary plate in terms of the number of slits detected and also to determine the peripheral velocity of the rotary plate in terms of the number of slits detected for a given length of time.

With conventional rotary encoders however, the detection of the peripheral velocity of the rotary plate is essentially such as to detect the angle of rotation from a position at which rotation of the rotary plate is initiated. The conventional rotary encoder is unable to detect the angle of rotation of the rotary plate from a specific reference angular position during the continued rotation of the rotary plate.

SUMMARY OF THE INVENTION

Accordingly, the present invention has been devised with a view to substantially eliminate the above discussed incapability inherent in prior rotary encoders and has for its essential object to provide an improved rotary encoder capable of detecting the angle of rotation of the rotary plate from the specific reference angular position.

In order to accomplish this and other objects of the present invention, there is provided, in accordance with the present invention, a rotary encoder which comprises a rotary plate having a plurality of primary slits defined in the rotary plate in a circular row coaxial with the axis of rotation of the rotary plate, said rotary plate also having at least one reference slit defined therein at a position radially of the circular row of the primary slits, a primary photoelectric detector including a source of light and a photo-sensor positioned one above the other with the circular row of the primary slits intervening therebetween, and an auxiliary photoelectric detector including a source of light and a photo-sensor positioned one above the other with the path of travel of the reference slit intervening therebetween.

According to the present invention, during the rotation of the rotary plate, the primary slits in the rotary plate can be successively detected by the first photoelectric detector whereas the passage of the reference slit can be detected by the auxiliary photoelectric detector.

BRIEF DESCRIPTION OF THE DRAWINGS

This and other objects and features of the present invention will become clear from the following description taken in conjunction with a preferred embodiment thereof with reference to the accompanying drawings, in which.

DETAILED DESCRIPTION OF THE EMBODIMENT

Figure 1:
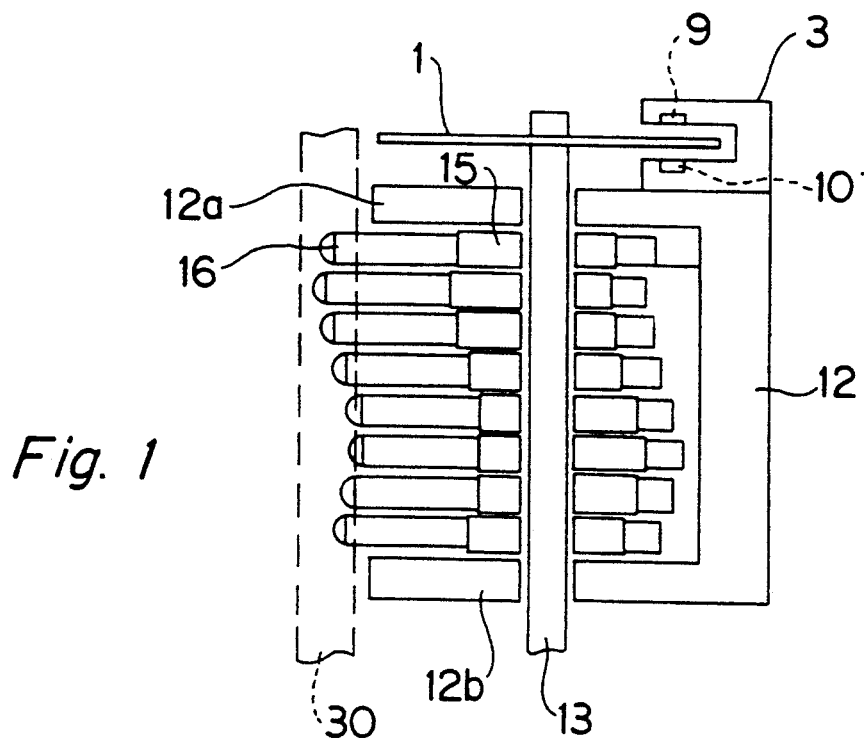
FIG. 1 is a schematic side sectional view of an infusion pump.
Figure 2:
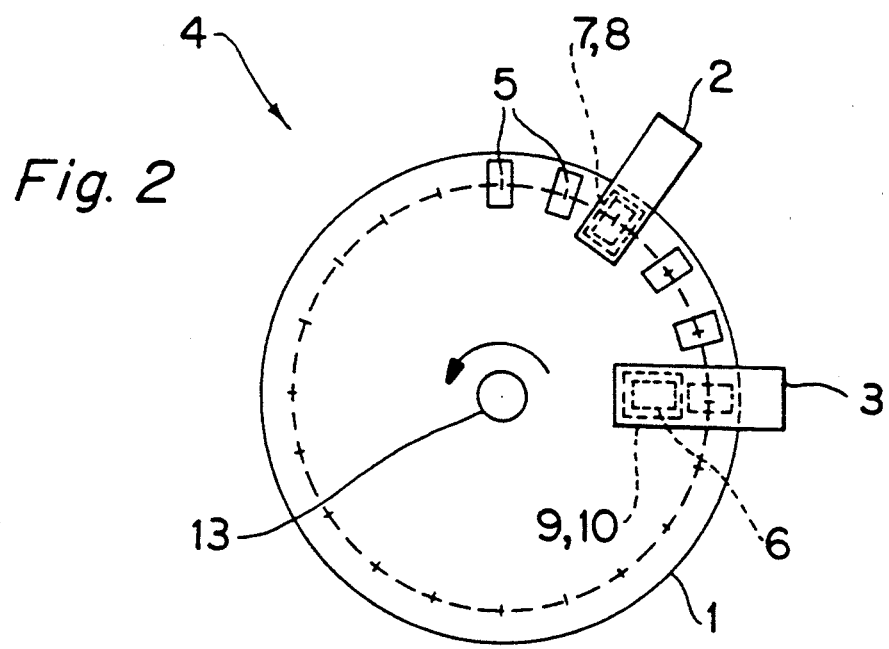
FIG. 2 is a schematic top plan view of a rotary encoder used in the infusion pump according to a preferred embodiment of the present invention.

Referring to the drawings, particularly to FIGS. 1 and 2, reference numeral 1 identifies a rotary disc and reference numerals 2 and 3 identifies primary and auxiliary photoelectric detectors, respectively. The rotary disc 1 and the first and second photoelectric detectors 2 and 3 constitute a rotary encoder 4, which is used in a parenteral solution infusion pump.

The rotary disc 1 has its outer peripheral portion formed with a plurality of primary slits 5 defined therein along a circular row in a circumferentially equally spaced relationship with each other and also with at least one reference slit 6 defined at a position radially inwardly of the circular row of the primary slits 5. The primary photoelectric detector 2 comprises a source of light 7 and a photo-sensor 8 disposed with the light source 7 and the photo-sensor 8 positioned above and beneath the circular row of primary slits 5, respectively. Similarly, the auxiliary photoelectric detector 3 comprises a source of light 9 and a photo-sensor 10 disposed with the light source 9 and the photo-sensor 10 positioned above and beneath the path of travel of the reference slit 6, respectively.

Both of the first and second photoelectric detectors 2 and 3 are mounted on and fixedly supported by a generally U-shaped housing 12 having upper and lower arms 12a and 12b connected together by means of a transverse body. A drive shaft 13, coupled at one end to an electrically driven motor 21 and at the opposite end to the rotary disc 1, extends rotatably, but axially non-movably, through the upper and lower arms 12a and 12b of the U-shaped housing 12. A stack of eccentric cam plates 15 is mounted on a portion of the drive shaft 13 situated between the upper and lower arms 12a and 12b of the housing for rotation together with the drive shaft 13, each of said eccentric cam plates 15 being integrated with a respective finger 16 which extends radially outwardly therefrom.

Figure 3:
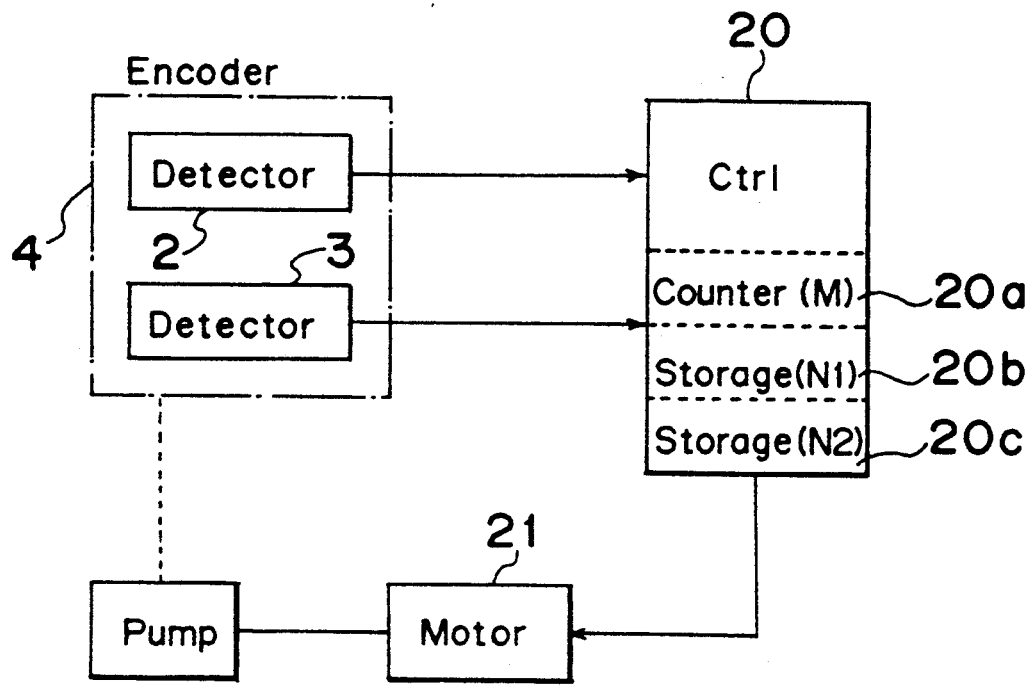
FIG. 3 is a block circuit diagram showing a control system coupled with the rotary encoder.

FIG. 3 shows block circuit diagram of a control system for the rotary encoder 4. A signal emerging from the primary photo-detector 2, which is indicative of any one of the primary slits 5 having traversed the path of light from the light source 7 towards the photo-sensor 8, and a signal emerging from the auxiliary photo-detector 3, which is indicative of the passage of the reference slit 6 across the path of light from the light source 9 towards the photo-sensor 10, are supplied to a control unit 20. The control unit 20 is so designed as to execute a predetermined control program in response to the application of the respective signals from the primary and auxiliary photo-detectors 2 and 3 thereto thereby to apply one of drive control signals of different states, as will be described in detail later, to the motor 21 coupled with the drive shaft 13.

Hereinafter, the operation of the system shown in and described with reference to FIGS. 1 and 2 will be described.

Reference numeral 30 shown in FIG. 1 represents a parenteral solution infusion piping having an upstream end fluid-coupled with an infusion bottle or bag and a downstream end fluid-coupled with a needle or catheter, a substantially intermediate portion of said infusion piping contactably positioned against the fingers 16. More specifically, the substantially intermediate portion of the infusion piping is so positioned relative to the fingers 16 that, during the rotation of the drive shaft 13 in one direction with the fingers 16 consequently successively driven outwards to press the substantially intermediate portion of the infusion piping in the order from the uppermost or upstream one of the fingers 16 down to the lowermost or downstream one of the fingers 16 while producing at least one moving zone of occlusion along said piping, an infusion liquid within the infusion piping can be successively conveyed from an upstream side down to a downstream side in a pulsating fashion. In other words, the infusion pump shown in FIG. 1 is of a construction effective to cause that portion of the solution infusion piping 30 to undergo a linear peristaltic motion to transport the infusion liquid successively towards the needle or catheter and then into a vascular system, for example, a vein, of a patient.

The infusion pump of a type employing similar fingers adapted to be successively driven by associated cam members is well known to those skilled in the art and is disclosed in, for example, the Japanese Laid-open Utility Model Publication No. 60-163938, published Oct. 31, 1985, reference to which is herein incorporated.

The infusion pump of the above described construction has a problem associated with the transportation of the infusion liquid through the infusion piping 30. Since the infusion liquid is transported in a pulsating fashion through that portion of the infusion piping 30, the amount of parenteral solution infusion liquid transported per stroke of each of the fingers 16 varies from the upstream side to the downstream side with respect to the direction of flow thereof towards the needle or catheter, with the minimum amount attained at the lowermost finger 16.

In view of the foregoing, the control unit 20 shown in FIG. 3 is so designed and so constructed as to execute the following sequence. Namely, the timing at which the uppermost finger 16 is driven to press the infusion piping 30 is controlled so as to match with the timing at which the auxiliary photo-detector 3 provides an output signal indicative of the passage of the reference slit 6 therethrough during the rotation of the rotary disc 1, while the number of output signals emerging from the primary photo-detector 2 and indicative of the number of the primary slits 5 detected thereby subsequent to the detection of the passage of the reference slit 6 past the auxiliary photo-detector 3 is counted. When the primary slits 5 having passed through the primary photo-detector 2 in a number corresponding to the angle of rotation of the rotary disc 1 which takes place during a period from the timing at which the uppermost finger 16 presses or squeezes the infusion piping 30 and shortly before the timing at which one of the fingers 16 which is spaced two fingers from the lowermost finger 16, that is, the third finger 16 counted backwards from the lowermost finger 16, presses or squeezes the infusion piping 30, are detected, a command necessary to increase the number of revolutions of the drive motor 21 is supplied to the motor 21 to accelerate a pressing action accomplished successively by the lowermost three fingers 16.

The increase of the number of revolutions of the drive shaft 13 so effected in the manner described above is terminated when the primary photo-detector 2 detects a passage thereacross of the primary slits 5 in a number corresponding to the angle of rotation of the rotary disc 1 which takes place during a period between the timing at which the uppermost finger 16 has squeezed the infusion piping 30 and the timing at which the third finger 16 referred to above squeezes the infusion piping 30.

In other words, according to the present invention, some of the fingers 16 positioned generally intermediate between one or some of the fingers 16, positioned upstream of the intermediate fingers 16, and one or some of the fingers positioned downstream of the intermediate fingers 16, for example, between the uppermost and the lowermost fingers 16 are driven to sequentially squeeze the infusion piping 30 at a higher speed than that at which any one of the uppermost or lowermost fingers 16 is driven. This can readily be understood from the chart shown in FIG. 5.

Thus, it will readily be understood that the primary slits 5 are successively detected by the primary photo-detector 2 comprised of the light source 7 and the photo-sensor while the reference slit 6 is detected by the auxiliary photo-detector 3 similarly comprised of the light source 9 and the photo-sensor 10 and that, therefore, it is possible to detect the angle of rotation at any position on the path of rotation of the rotary plate with the utilization of the output signal from the auxiliary photo-detector 3 indicating the passage of the reference slit 6 as a reference.

More specifically, the control unit 20 includes, as shown in FIG. 3, a counter 20a and a storage means including first and second signal storages 20b and 20c, all built therein. The counter 20a is utilized to count, and generate a count signal M indicative of, the number of the signals generated from the primary photo-detector 2 as a result of the successive passage of the primary slits 5 across the optical path between the light source 7 and the photo-sensor 8 during each rotation of the rotary disc 1.

The first storage 20b stores a first parameter N1 representative of a first predetermined number of primary slits 5 which would be counted during a period subsequent to the timing at which the uppermost one of the fingers 16 is driven to press the infusion piping 30 and prior to the timing at which a first arbitrarily chosen one of the remaining fingers 16 during each rotation of the rotary disc 1 is driven to press the infusion piping 30 at a first position spaced from a portion of the infusion piping 30 pressed by the uppermost finger 16.

The second storage 20c stores a second parameter N2 representative of a second predetermined number of the primary slits 5 which would be counted during a period subsequent to the timing at which the uppermost finger 16 is driven to press the infusion piping 30 and prior to the timing at which a second arbitrarily chosen one of the remaining fingers 16 during each rotation of the rotary disc 1 is driven to press the infusion piping 30 at a second position downstream of the first position with respect to the direction of flow of the fluid towards the injection needle.

Figure 4:
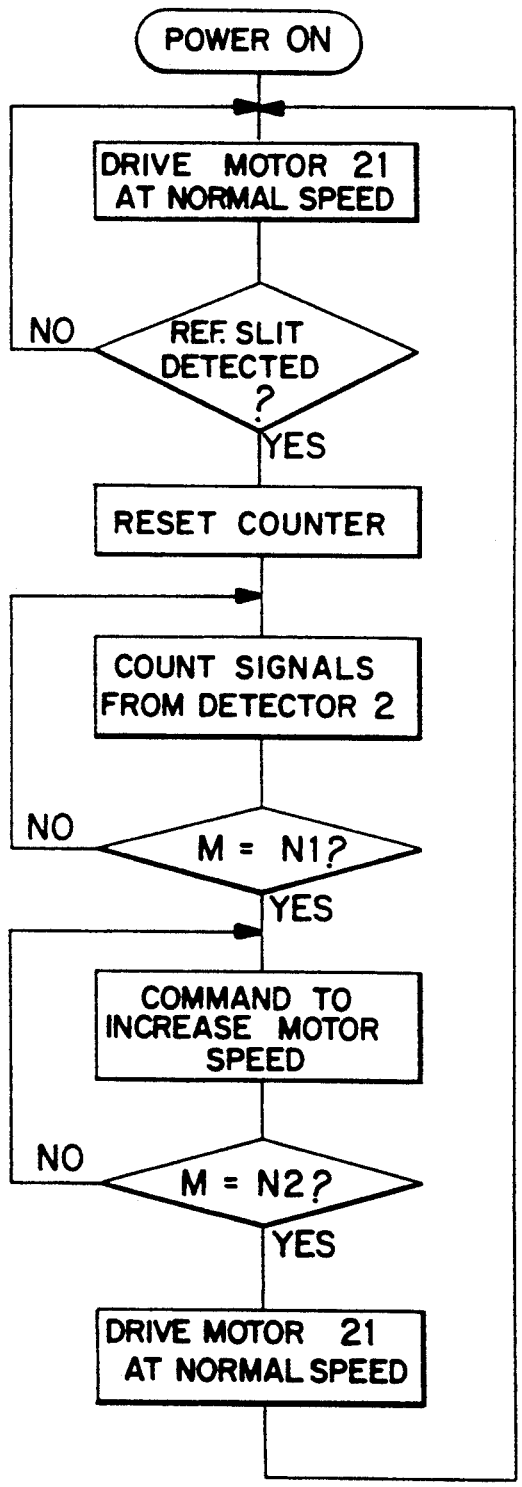
FIG. 4 is a flowchart showing the sequence of operation of the control system.

As can readily understood from the flowchart shown in FIG. 4, the control unit 20 also includes a first comparator for comparing the count signal M with the first parameter N1 and a second comparator for comparing the count signal M with the second parameter N2. In the event that the count signal M coincides with the first parameter N1 stored in the first storage 20b, the control unit 20 can generate a first drive control signal necessary to allow the motor to be driven at an increased speed. However, in the event that the count signal M subsequently coincides with the second parameter N2 stored in the second storage 20c, the control unit can generate a second control signal necessary to allow the motor to resume a normal speed.

Figure 5:
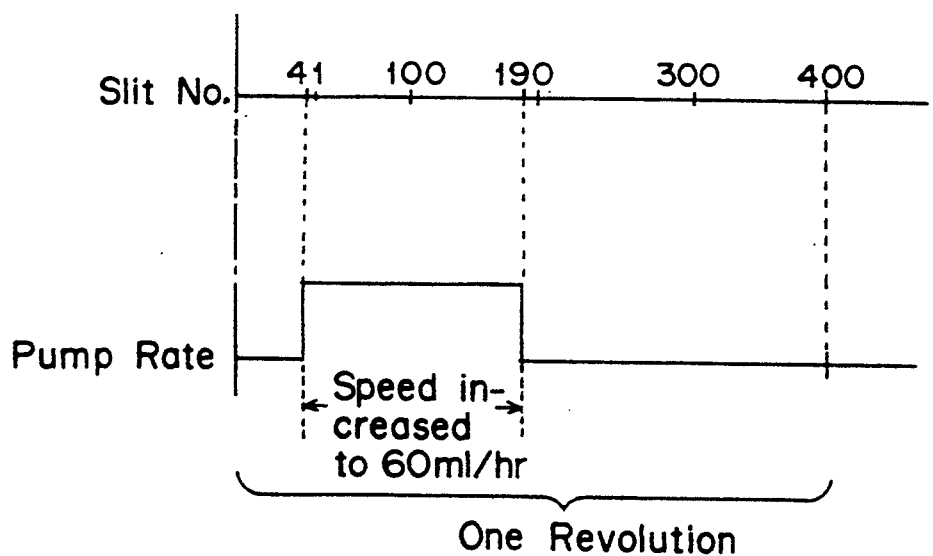
FIG. 5 is a chart showing an example of how the flow of the fluid is increased by the control system.

FIG. 5 illustrates an exemplary chart showing how the flow of the infusion solution through the piping 30 is controlled across the pump assembly of the construction described hereinbefore. In this example, the rotary disc 1 is assumed to have the 400 primary slits 5 defined therein. During each revolution of the motor-coupled drive shaft 13, the flow is increased when the primary detector 2 has detected the passage of a number of, for example, 41, primary slits 5 subsequent to the start of rotation of the drive shaft 13 and is caused to resume an initial value when and after the primary detector 2 has detected the passage of 190 primary slits 5 subsequent to the start of rotation of the drive shaft 13. The first and second parameters N1 and N2 described as stored respectively in the first and second storages 20b and 20c, corresponds to the count of the 41 primary slits 5 and the count of the 190 primary slits 5 shown in FIG. 5.

For this purpose, the control unit 20 is so programmed as to operate in the following manner.

As shown in FIG. 4, subsequent to the start of the program flow, the drive motor 21 is electrically powered to drive the drive shaft 13 at a predetermined normal speed (required to accomplish the flow of the infusion fluid at, for example, 2.1 to 22.0 ml/hr) accompanied by a rotation of the rotary disc 1. When the auxiliary detector 3 detects the passage of the reference slit 6, the counter 20a built in the control unit 20 is reset to zero so that the counter 20a can start its counting operation to count the number of the signals fed from the primary detector 2, i.e., to count the number of the primary slits 5 having passed across the primary detector 2 while generating the count signal. Should the count of the counter 20a subsequently coincides with the first parameter N1 stored in the first storage 20b and indicative of the first predetermined number of, for example, 41, primary slits 5, the control unit 20 generates the drive control signal of the first state to the drive motor 21 to increase the speed of rotation of the drive shaft 13 so that the flow of the infusion fluid through the piping can be increased to, for example, 60.0 ml/hr.

The drive of the drive shaft 13 at the increased speed continues until the count of the counter 20a is incremented to a value coinciding with the second parameter N2 stored in the second storage 20c and indicative of the second predetermined number of, for example, 190, primary slits 5. Once the count of the counter 20a has shown the value equal to the second parameter N2, the control unit 20 generates the drive control signal of the second state to the drive motor 21 to cause the drive shaft 13 to assume the normal initial speed.

By the foregoing control performed in the practice of the present invention, the time during which the amount of the parenteral solution infusion liquid transported by the lowermost finger 16 is reduced can be advantageously shortened, thereby relieving a pulsating phenomenon of flow of the infusion liquid.

Although the present invention has been fully described in connection with the preferred embodiment thereof with reference to the accompanying drawings, it is to be noted that various changes and modifications are apparent to those skilled in the art. By way of example, although the primary and auxiliary photo-detectors have been shown and described as used separate from each other, the both may be integrated together. When both detectors are integrated, a single light source may be employed for both of the primary and auxiliary photo-detectors.

Such changes and modifications are to be understood as included within the scope of the present invention as defined by the appended claims unless they depart therefrom.

What is claimed is:

1. A parenteral solution infusion pump comprising:
   a peristaltic pump infusing a flow of fluid along a piping from a source of fluid to a destination;
   a rotary encoder for controlling said pump said rotary encoder including,
   (a) a rotary plate having a plurality of primary slits defined therein in a circular row coaxial with an axis of rotation of the rotary plate, said rotary plate also having at least one reference slit defined therein at a position radially of the circular row of the primary slits;
   (b) a primary detector aligned with the circular row of the primary slits detecting the presence of one of said primary slits as the rotary plate rotates; and
   (c) an auxiliary detector physically separate from said primary detector positioned along the path of travel of the reference slit detecting the reference slit as the rotary plate rotates;
   (d) drive means for controlling the speed of the peristaltic pump and thereby rotational speed of said rotary plate;
   (e) memory means for storing a plurality of parameters indicating the total number of primary slits for a given time during one revolution of said rotary disc corresponding to a particular pump speed;
   (f) a counter for counting the total number of primary slits detected by said primary detector, said counter initiating counting upon detection of said reference slit by said auxiliary detector;
   (g) comparator means for comparing the total number of primary slits with a selected one of said parameters stored in said memory means and for causing the drive means to increase the speed of the peristaltic pump if the total number of primary slits counted is less than the corresponding parameter, thereby maintaining a constant fluid flow within the piping.

2. A parenteral solution infusion system comprising:
   peristaltic means including a stack of finger members adapted to be sequentially driven to operatively engage a piping to sequentially squeeze said piping while producing at least one moving zone of occlusion along said piping for infusing a fluid from a source of fluid towards a destination;
   drive means for driving said peristaltic means to sequentially drive the finger members;
   a rotary encoder electrically coupled with the drive means and including;
   (a) a rotary plate having a plurality of primary slits defined therein in a circular row coaxial with an axis of rotation of the rotary plate, said rotary plate also having at least one reference slit defined therein at a position radially of the circular row of the primary slits and coinciding with the timing at which one of the finger members positioned on a most upstream side with respect to the direction of flow of the fluid from the fluid source is driven to squeeze the piping;

(b) a primary photoelectric detector including a primary source of light and a primary photo-sensor positioned one above the other with the circular row of the primary slits intervening therebetween, said primary photoelectric detector generating a primary signal each time any one of the primary slits traverses an optical path between the primary light source and the primary photo-sensor; and (c) an auxiliary photoelectric detector physically separate from said primary photoelectric detector and including an auxiliary source of light and an auxiliary photo-sensor positioned one above the other with the path of travel of the reference slit intervening therebetween, said auxiliary photoelectric detector generating an auxiliary signal indicative of a passage of the reference slit across an optical path between the auxiliary light source and the auxiliary photo-sensor; and control means for applying one of at least two drive control signals to said drive means and including;

(a) a first storage means storing a first parameter representative of the number of primary slits which would be counted during a period subsequent to the timing at which said one of the slits squeezes the piping and prior to the timing at which a first predetermined one of the remaining finger members squeezes the piping:

(b) a counting means for counting, and generating a count signal indicative of, the number of the primary signals generated from the primary photoelectric detector subsequent to a detection of the passage of the reference slit by said auxiliary photoelectric detector; and (c) a first comparing means for comparing the count signal with the first parameter, said first comparing means causing the control means to generate said one of the drive control signals, in the event that said count signal coincides with the first parameter, thereby to accelerate said drive means for a predetermined length of time.

3. The parenteral solution infusion system as claimed in claim 2, wherein said control means further includes;

(d) a second storage means storing a second parameter representative of the number of primary slits which would be counted during a period subsequent to the timing at which said one of the slits squeezes the piping and prior to the timing at which a second predetermined one of the remaining finger members squeezes the piping, said second predetermined one of the remaining finger members being positioned downstream of said first predetermined finger member with respect to the direction of flow of the fluid; and (d) a second comparing means for comparing the count signal with the second parameter, said second comparing means causing the control means to generate the other of the drive control signals, in the event that said count signal coincides with the second parameter, thereby to cause said drive means to assume an initial speed.

* * * * *